United States Patent
Narula

(10) Patent No.: US 12,157,909 B2
(45) Date of Patent: Dec. 3, 2024

(54) APPARATUS FOR MICROBIAL ACTIVITY DETECTION AND INVENTORY MANAGEMENT, AND PROCESS THEREOF

(71) Applicant: Poonam Narula, Sunnyvale, CA (US)

(72) Inventor: Poonam Narula, Sunnyvale, CA (US)

( * ) Notice: Subject to any disclaimer, the term of this patent is extended or adjusted under 35 U.S.C. 154(b) by 978 days.

(21) Appl. No.: 17/264,992

(22) PCT Filed: Aug. 2, 2019

(86) PCT No.: PCT/US2019/044901
§ 371 (c)(1),
(2) Date: Feb. 1, 2021

(87) PCT Pub. No.: WO2020/033263
PCT Pub. Date: Feb. 13, 2020

(65) Prior Publication Data
US 2021/0310037 A1    Oct. 7, 2021

Related U.S. Application Data

(60) Provisional application No. 62/715,499, filed on Aug. 7, 2018.

(51) Int. Cl.
*C12Q 1/04*     (2006.01)
*G01N 31/22*    (2006.01)
*G01N 33/02*    (2006.01)

(52) U.S. Cl.
CPC ............. *C12Q 1/04* (2013.01); *G01N 31/223* (2013.01); *G01N 33/02* (2013.01)

(58) Field of Classification Search
CPC ........ C12Q 1/04; G01N 31/223; G01N 33/02; G01N 15/14; G01N 21/6428; G01N 21/645; G01N 21/76; B01L 2300/0654
See application file for complete search history.

(56) References Cited

U.S. PATENT DOCUMENTS

| 4,003,709 A | 1/1977 | Eaton et al. |
| 4,659,550 A | 4/1987 | Schildknecht |

(Continued)

FOREIGN PATENT DOCUMENTS

| CN | 207115219 U | 3/2018 |
| EP | 3168608 A1 | 5/2017 |

(Continued)

OTHER PUBLICATIONS

Sousa, A.R. et al.; "Determination of the respiration rate parameters of cherry tomatoes and their joint confidence regions using closed systems," Journal of Food Engineering, 2017, pp. 12-22, vol. 206.

(Continued)

*Primary Examiner* — Michael L Hobbs
(74) *Attorney, Agent, or Firm* — Casimir Jones, SC; Tristan A. Fuierer

(57) ABSTRACT

A system and method for the real time determination of microbial growth in or on perishable products. The system can predict the extent of microbial growth, e.g., whether food is spoiled, in real time by measuring chemicals released, e.g., $CO_2$, from the perishable product during microbial growth. The output from a sensor can be correlated to the extent of microbial growth, i.e., spoilage, and provide information about the extent of microbial growth to the user, for example, through their smart devices.

20 Claims, 4 Drawing Sheets

(56) References Cited

U.S. PATENT DOCUMENTS

| | | |
|---|---|---|
| 6,453,687 B2 | 9/2002 | Sharood et al. |
| 7,372,003 B2 | 5/2008 | Kates |
| 8,449,834 B2 | 5/2013 | Ostrowski et al. |
| 8,933,210 B2 | 1/2015 | Lu et al. |
| 9,989,474 B2 | 6/2018 | Song et al. |
| 10,157,340 B2 | 12/2018 | Swager et al. |
| 10,185,733 B2 | 1/2019 | Knobel |
| 10,203,678 B2 | 2/2019 | Lagares-Greenblatt et al. |
| 10,215,644 B2 | 2/2019 | Lawler, Jr. |
| 10,247,713 B2 | 4/2019 | Smyth et al. |
| 10,267,667 B2 | 4/2019 | Gurumohan et al. |
| 10,286,368 B2 | 5/2019 | Deshpande |
| 10,289,612 B2 | 5/2019 | Knobel |
| 10,320,582 B1 | 6/2019 | Wallace et al. |
| 10,323,982 B2 | 6/2019 | Goldring et al. |
| 10,324,042 B2 | 6/2019 | Heacock |
| 10,324,439 B2 | 6/2019 | Lagares-Greenblatt et al. |
| 10,326,537 B2 | 6/2019 | Johansen |
| 10,332,421 B2 | 6/2019 | Minvielle |
| 10,338,048 B2 | 7/2019 | La Valle Sansone et al. |
| 2004/0077075 A1* | 4/2004 | Jensen .................... C12M 23/16 435/297.5 |
| 2005/0153052 A1 | 7/2005 | Williams et al. |
| 2005/0254055 A1* | 11/2005 | Peng ....................... C12M 41/36 356/432 |
| 2005/0266516 A1* | 12/2005 | Kanipayor ............... C12Q 1/04 435/287.1 |
| 2006/0096871 A1 | 5/2006 | Manoukian et al. |
| 2007/0176773 A1 | 8/2007 | Smolander et al. |
| 2007/0222973 A1 | 9/2007 | Hoshiko et al. |
| 2007/0285238 A1 | 12/2007 | Batra |
| 2008/0040272 A1 | 2/2008 | Eskin |
| 2008/0176273 A1 | 7/2008 | Eden et al. |
| 2011/0104738 A1 | 5/2011 | Forsell |
| 2013/0293894 A1 | 11/2013 | Salerno et al. |
| 2017/0089935 A1* | 3/2017 | Eden ....................... C12Q 1/18 |
| 2017/0241930 A1 | 8/2017 | Roberts |
| 2021/0246643 A1 | 8/2021 | Sonovani |

FOREIGN PATENT DOCUMENTS

| | | |
|---|---|---|
| WO | 2013096243 A1 | 6/2013 |
| WO | 2018116294 A1 | 6/2018 |

OTHER PUBLICATIONS

Fonseca, Susana C., et al.,; "Modelling respiration rate of fresh fruits and vegetables for modified atmosphere packages: a review," Journal of Food Engineering, 2002, pp. 99-119, vol. 52.

International Search Report, PCT/US19/44901, dated Oct. 24, 2019.

\* cited by examiner

APPARATUS FOR MICROBIAL ACTIVITY DETECTION AND INVENTORY MANAGEMENT, AND PROCESS THEREOF

CROSS-REFERENCE TO RELATED APPLICATIONS

This application is filed under the provisions of 35 U.S.C. § 371 and claims the priority of International Patent Application No. PCT/US2019/044901 filed on 2 Aug. 2019 entitled "APPARATUS FOR MICROBIAL ACTIVITY DETECTION AND INVENTORY MANAGEMENT, AND PROCESS THEREOF" in the name of Poonam NARULA, which claims priority to U.S. Provisional Patent Application No. 62/715,499, filed on 7 Aug. 2018, both of which are hereby incorporated by reference herein in their entirety.

STATEMENT OF PRIORITY

This application claims priority to U.S. Provisional Application No. 62/715,499 filed on Aug. 7, 2018, the contents of which are incorporated by reference herein for all purposes.

TECHNICAL FIELD

The present invention relates to a system and method for the real time determination of food spoilage.

BACKGROUND

It is estimated that 40% of the food supply in the United States is wasted. This waste, according to the USDA, is estimated at 130 billion tons of food per year, at a cost of $160 billion per year. On Oct. 18, 2018, the USDA, EPA and FDA signed a joint agreement entitled Winning on Reducing Food Waste Initiative, which aims to reduce food waste in the US by 50% by 2030. According to the United Nations Food and Agriculture Organization, the world population will have an additional 2 billion people by 2050 and this population explosion will require an optimization of the resources so that food insecurity, malnutrition and the effects of greenhouse gas emissions and fresh water consumption associated with food waste are minimized.

The term "perishable" is used to refer to products that are subject to spoilage or decay. The companies that make and/or sell these products, and the consumers that use them, are presented with the continuing problem of identifying which products have exceeded their shelf-life, especially when the perishable products are starting to spoil or otherwise lose their effectiveness Manufacturers of perishable goods date code their products so that, either through sale or consumption by the purchaser, the products will be limited to a reasonable, measurable shelf life. Some perishable products are visually inspected to predict spoilage. Disadvantageously, these methods result in a large amount of waste since they employ an empirical determination of spoilage status.

There exist many known indicators of freshness of food products that indicate whether a certain food product may be spoiled. One of the prime indicators of food spoilage is microbial growth. On the other hand, some bacteria do not cause spoilage, but are actually added to milk or cream after pasteurization to make "cultured" products such as certain hard cheese. In those cases, spoilage would be measured by looking for common pathogenic indicators such as *salmonella* or *E. coli* 0157. Even though the strictest standards of care may be observed in the preparation, packaging, scaling, and sterilization of foodstuffs and their containers, it is virtually impossible to insure completely against the occasional presence of bacteria.

While alternatives to strict production and shelf life controls have been explored, there has been surprisingly little visible progress with respect to other solutions for identifying food spoilage. One such alternative solution, as suggested by the present invention, would be a system and method for the real time determination of food spoilage which would allow the user of the system to readily and quickly identify the condition of the food within the container (e.g., good or bad/spoiled). From an economic standpoint, a reliable and inexpensive detection system could well eliminate the need for shelf life controls, thus reducing or eliminating losses from the disposal of perfectly good food products.

Towards this end, a $CO_2$ detection-based system to monitor the freshness of a perishable products and method of using same is described herein to reduce food waste. The system can predict the status of food freshness in real time by measuring chemicals released during food spoilage. The output from the chemical sensor can be correlated to the extent of spoilage and provide information to the user, for example, through their smart devices. The information can allow a user to make informed decisions about food consumption based on the freshness indicator. This system and method can have economies of scale and can be utilized by everyone in the food supply value chain, e.g., farms, processors, distributors, and storage as well as in retail stores, food service operations, and households.

SUMMARY

In one aspect, a system for detecting microbial growth on or in a specific perishable product in real time is described, said system comprising:
 (A) a chemical sensor comprising a cuvette holder for the positioning of a cuvette, wherein the chemical sensor is capable of sensing a byproduct of microbial growth;
 (B) a detection device for measuring at least one characteristic of said chemical sensor and converting the measured characteristic into an electrical signal;
 (C) a digital output device capable of receiving the electrical signal from the detection device and algorithmically analyzing the electrical signal; and
 (D) an output display, wherein results of the analysis performed by the digital output device are provided to a user, wherein the results convey to the user the extent of microbial growth of the perishable product.

In another aspect, a method for detecting microbial growth on or in a perishable product in real time is described, said method comprising:
 (I) positioning a chemical sensor and a detection device in a location proximate to the perishable product;
 (II) measuring at least one characteristic of microbial growth on or in the perishable product using the chemical sensor in cooperation with the detection device;
 (III) converting at least one characteristic of microbial growth to digitized data;
 (IV) transmitting the digitized data to a digital output device;
 (V) algorithmically analyzing the digitized data to determine the extent of microbial growth on or in the perishable product; and (VI) displaying the extent of microbial growth on an output display to inform a user if the perishable product should be disposed of or sterilized.

Other aspects, features and embodiments of the invention will be more fully apparent from the ensuing disclosure and appended claims.

BRIEF DESCRIPTION OF THE DRAWINGS

The several objects, features, and advantages of this invention will be understood by reading this description in conjunction with the drawings, in which.

DETAILED DESCRIPTION

Figure 1:
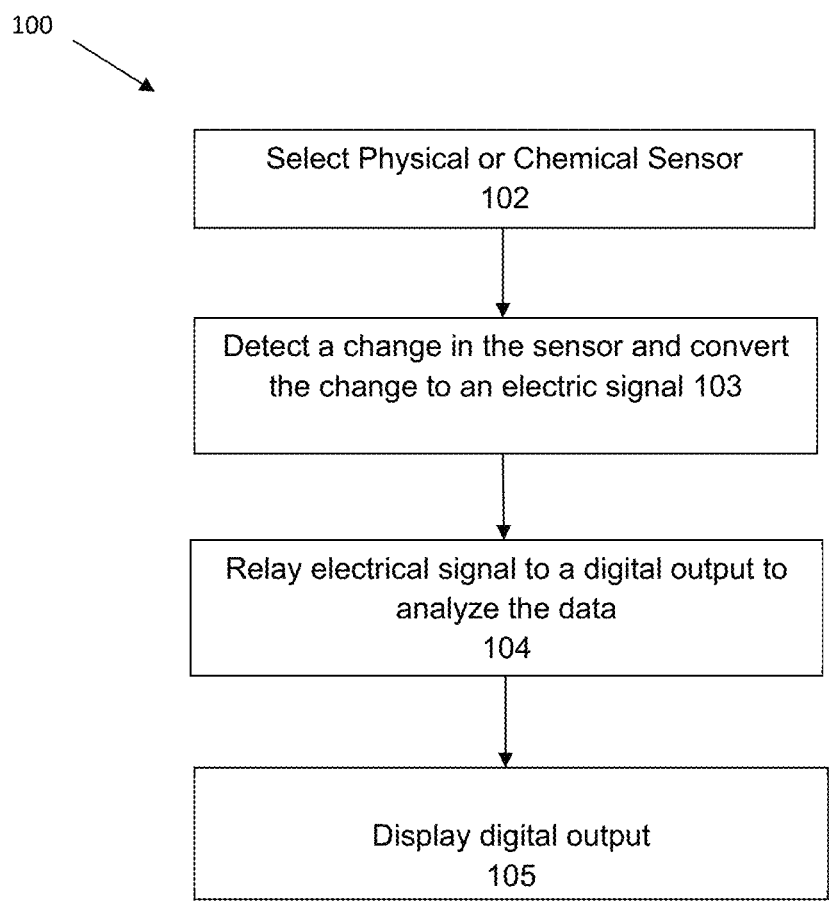
FIG. 1 is a flow chart of a generalized microbial growth detection system 100 described herein.

The present invention relates to a system and method for the real time determination of microbial growth in or on perishable products. The system can predict the extent of microbial growth, e.g., whether food is spoiled, in real time by measuring chemicals released, e.g., $CO_2$, during microbial growth. The output from the sensor can be correlated to the extent of microbial growth, i.e., spoilage, and provide information to the user, for example, through their smart devices.

Under normal packing conditions, when a food product within a sealed container or package starts to spoil, several byproducts are formed and they accumulate therein. It is theoretically possible to detect spoilage of perishable products by detecting one or more spoilage by-products. Common to all such deterioration is the production of heat, acidity, pressure, and carbon dioxide ($CO_2$). Under packing conditions, microbes thrive during storage of food products and result in the formation of many chemical species including, but not limited to, lactic acid and acetic acid by lactic acid bacteria. Carbon dioxide is also known to be produced during any kind of bacterial or mold growth on foods. Ideally, a spoilage detector should be useable with as many different food products as possible, without requiring different detectors for each different type of perishable item.

The prior art evidences that heat and pressure are not practical ways to detect food spoilage Chemicals that change color when pH changes have been used to mark the presence or absence of bacterial growth. Commonly utilized pH indicators include phenol red, bromocresol blue, and neutral red. Markers, such as electrical impedance, electrical conductivity, and the amount of ATP (adenosine triphosphate), have been measured from microbes growing in a general medium with the addition of a chemical that is measured. Tests for the above-mentioned markers can be accurate but are not practical and/or are expensive and unable to identify food spoilage in real time.

It is possible to detect carbon dioxide gas, a by-product of bacteria, to indicate the likelihood that the perishable product is deteriorating. Such a detector would be usable with the widest possible variety of perishable products. Such a detector would have to operate independently of the other properties of products, such as pH, salt content (corrosiveness), pressure and/or vacuum. Further, such a detector must be approved for use in connection with consumables and is preferably inexpensive to produce and easy to use.

U.S. Pat. No. 4,003,709 to Eaton et al teaches providing a liquid impermeable pouch in which a liquid carbon dioxide detecting solution is entrapped. The solution provides a visually observable change when the concentration of carbon dioxide rises substantially above that which is the normal ambient concentration for our atmosphere. A suitable opening is formed in a container and the pouch is sealed into and over the opening so that the inert plastic material seals the opening and the microporous plastic portion is inside the container in gaseous communication with the food contents. If carbon dioxide gas is generated within the container, e.g., as a result of deterioration of the food, the $CO_2$ will pass through the microporous plastic and react with the calcium hydroxide to precipitate calcium carbonate. This causes the solution to change from clear to milky white, and this change is readily observable from outside the container by looking through the window. Disadvantageously, turbidity is practical only for consumers with trained eyes or when expensive and bulky spectrophotometers are used. Furthermore, just because the solution in the pouch of U.S. Pat. No. 4,003,709 became turbid does not necessarily mean that the product is spoiled, which could result in the disposal of perishable product that is still safe to consume or use.

As defined herein, "perishable" or "perishables" is used to refer to products that are subject to spoilage or decay on or in said products. Perishable products comprise anything that is capable of supporting microbial growth including, but are not limited to, chilled and minimally processed foods and beverages, fresh produce, precut produce, cooked food, uncooked food, dairy products (e.g., milk, cheese), grains, meat, poultry, oils, waxes, roots, nuts, seafood, pharmaceuticals, supplements, solutions, ayurvedic remedy, pharmaceuticals, blood, beauty and hygiene products, medical aids (e.g., bandages, etc.), and medical devices, each of which has its own unique shelf-life. It also includes wounds on living matter, such as human beings, animals or on plants. Wounds can include, for example cuts, scrapes, stings, or any other format that exposes the surface that undergoes a healing process. The perishable products can be stored in environments appropriate for maintaining the usefulness of said product. Furthermore, the perishable products can be anywhere in the value chain, e.g., from farm-to-fork for food products. It should be appreciated by the person skilled in the art that reference to a perishable product can indicate that only one product is present for testing, e.g., just strawberries in a refrigerator, or at least two perishable products are present for testing, e.g., strawberries and blueberries in a refrigerator.

As defined herein, a "sensor" includes a device or system that can detect chemical or physical changes associated with microbial growth or microbial decay, and include for example, the detection of at least one of carbon dioxide, oxygen, ethylene, hydrogen sulfide, ammonia, volatile and non-volatile amines, total volatile nitrogen, volatile acids and bases, non-volatile acids and bases, slime formation, *E. coli, Salmonella*, and *Listeria monocytogenes*.

As used herein, "shelf life status" is calculated by measuring a parameter that is the characteristic of the detection system including, but not limited to, Nephelometric Turbidity Units (NTU), milkiness, turbidity, opalescence, redox potential change, light intensity change, and color change.

As defined herein, "biopharmaceuticals" include, but are not limited to, antibodies, proteins, peptides, nucleic acids, polysaccharides, and combinations thereof.

Cuvettes are well known in the spectrophotometric arts, but as used herein, a "cuvette" is meant to describe a container that holds the chemical sensor or chemical sensor species. It should be appreciated that the cuvette can be of any shape or size, as required for the system and the location that said system will be positioned. Cuvette shapes contemplated include, but are not limited to, circular cylinders, cubic squares, rectangular parallelepiped shapes, polygonal prisms (e.g., triangular prisms, pentagonal prisms, hexagonal prisms), hemispheric shapes, semi-ellipsoid shapes, and cylindrical discs.

As used herein, a "medical device" is an instrument, apparatus, material, or other article, whether used alone or in combination, including software necessary for its application, intended by the manufacturer to be used for human beings for diagnosis, prevention, monitoring treatment, or alleviation of disease; diagnosis, monitoring, treatment, or alleviation of or compensation for an injury or handicap; investigation, replacement, or modification of the anatomy or of a physiologic process; or control of conception, and that does not achieve its primary intended action in or on the human body by pharmacologic, immunologic, or metabolic means but might be assisted in its function by such means. A medical device includes, without limitation, a surgical instrument, a respiratory therapy instrument, an anesthesia instrument, a catheter, an implant, a probe, an endoscope, an arthroscope, a laparoscope, a blade, a cystoscope, a spirometer, a CPAP mask and tubing, dialysis instrument and accessories, a heart-lung machine and accessories, a heart-lung bypass machine and accessories, and a diaphragm fitting ring. Non-limiting examples of a probe includes an ultrasound probe and an esophageal manometry probe. Non-limiting examples of a catheter includes a cardiac catheter, an urinary catheter, an anorectal manometry catheter. Non-limiting examples of an endoscope includes a gastrointestinal endoscope, a bronchoscope, and a nasopharyngoscope. Non-limiting examples of a blade includes a laryngoscope blade.

As used herein, "artificial intelligence" or "AI" corresponds to intelligence demonstrated by machines, in contrast to the natural intelligence displayed by humans. As used herein, AI is used to describe machines (or computers) that mimic "cognitive" functions that humans associate with the human mind, such as "learning" and "problem solving". In the present case, AI refers to Analytical AI having characteristics consistent with cognitive intelligence, generating cognitive representation of the world, and using learning based on past experience to inform future decisions.

As used herein, the term "blockchain" refers to a time-dependent growing list of immutable informational objects or records (hereinafter referred to as "blocks") that are linked via cryptography. As used herein, the term "timestamp" refers to a sequence of characters or encoded information identifying when a certain event occurred. The timestamp includes digital date and time information that can be attached to the block. As used herein, the terms "hash" or "hash value" refer to a value resulting from a hash function, which is a function used to map certain data having an arbitrary size to data of a finite size. The hash is a unique identifier associated to a block, and is a key element of the distributed validated system described here. Typically, each block is associated with a timestamp, a hash of the then current block, and a hash associated with the immediately recent block of the then current block.

As used herein, "in situ" is understood to correspond to the chemical or physical sensing of the relevant byproducts in the location where the system is positioned. For example, the system may be positioned in a chamber or the system may be positioned in proximity to a wound.

As defined herein, a "chamber" includes, but is not limited to, a refrigerator (commercial or residential), a freezer (commercial or residential), a cooler, a package truck, a package, a carton, a box, a shipping container, a pantry, metal cans, plastic bottles, plastic containers, plastic bags, glass containers, glass bottles, paper containers (waxed or unwaxed), a shelf, a wine cellar, a dehydrator, a medical device storage unit, a medical probe storage unit, an oil container, and storage rooms.

As defined herein, a "smart device" includes, but is not limited to, a smartphone, tablet, laptop or other computing device. Smart devices can be wired- or wireless-enabled, and can automatically discover, and pair with a plurality of other wireless-enabled devices.

As used herein, a "photoresistor" is intended to be synonymous with a "phototransistor," a "light-dependent resistor (LDR)," and a "photo-conductive cell," each one being a light-controlled variable resistor.

As used herein, "turbidity" is intended to be synonymous with "opacity."

As used herein, "microbial activity" refers to a physical change or a chemical change on or in the perishable product. Physical change includes, but is not limited to, a change in temperature, pressure, shape, size, color or growth of living organisms (e.g., bacteria, fungus, etc.). Chemical change includes, but is not limited to, the evolution of carbon dioxide, oxygen, *E. coli, salmonella, listeria*, volatile acids and bases, non-volatile acids and bases, slime formation, volatile and non volatile amines, or growth of living organisms (bacteria, fungus, etc.). It should be appreciated that microbial activity can result in microbial growth on or in the perishable product, which can eventually lead to spoilage and/or a requirement that the perishable product, e.g., a medical device, be thoroughly sterilized before further use.

The terms "good" and "bad" pertaining to ingestible products are understood to mean the product can be consumed or should not be consumed, respectively. As used herein, "bad" and "spoiled" are intended to be synonymous.

The present invention relates broadly to the detection of species that are by-products of microbial decay. The by-products of microbial decay can be a reactant in a chemical reaction, whereby the products of the chemical reaction are detectable. Once the information from the detector is discerned, the information can be analyzed, digitized and transmitted to a data processing unit and/or digital receiver, such as, for example, a wireless device, computer, phone, or other data processing or communication device. Using the system and method described herein, once an unacceptable amount of microbial decay has been detected, as evidenced by an amount of byproduct sensed by the chemical sensor, the perishable product should be disposed of.

Notably, the present invention does not relate to a food storage device management system to assist a person with finding the storage location of a certain food in their storage devices (e.g., where the milk is located in their the refrigerator), nor does the present invention rely on visual indicators such as photographic and/or video images to determine if the food looks as though it is of low quality. In fact, taking a picture or video to conclude that the food is of low quality disregards the fact that the food may still be consumable. The present invention relates to the reduction of food waste, wherein the metric for disposal is microbial growth, not that the banana looks brown, i.e., of low quality. Accordingly, the system and method of using same does not require the use of video or photographs to identify microbial growth on or in the perishable product.

Broadly, referring to FIG. 1, the microbial growth detection system 100 described herein comprises a physical or chemical sensor 102, a detection system capable of identifying a change of the respective sensor (e.g., change in turbidity or opacity) and converting the change into an electrical signal (e.g., emf or frequency) 103, a system that relays the electrical signal from the detection system to a digital output for analysis 104, and a display of the results of the analysis of the digital output 105 so as to communicate to a user the extent of microbial growth (i.e., is the perishable product spoiled or not). The microbial growth detection system can provide quantitative and/or qualitative results relating to microbial activity on or in a perishable product as well as convey activity data in formats for decision making. This system and method can be used in every aspect of the perishable product value chain, as a way to detect byproducts of microbial growth and thus indicators of integrity, for perishable product waste reduction, for product tracking, for automated inventory management, for inventory management in places with restricted visibility like vending machines, and freezers and large refrigerators. The system and method of using same can also be used for item level tagging for monitoring shelf life and compliance with safety as well as in dressing wounds in medical applications.

Figure 2A:
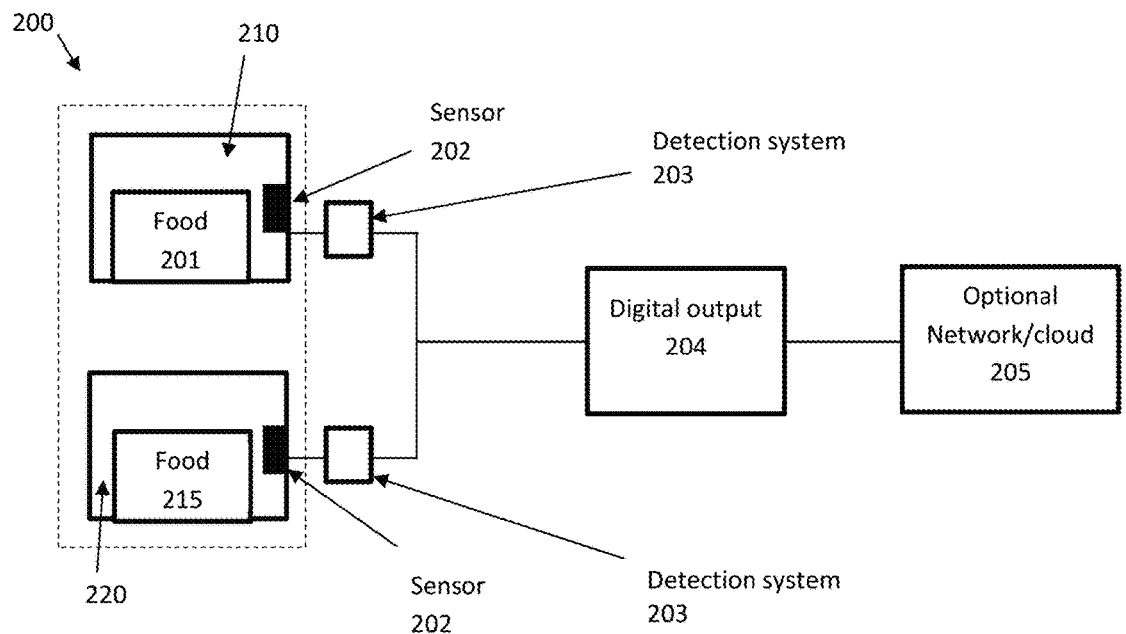
FIG. 2A is a schematic of an embodiment of the microbial growth detection system, or Microbial Activity Detection (MAD) (200) described herein.
Figure 2B:
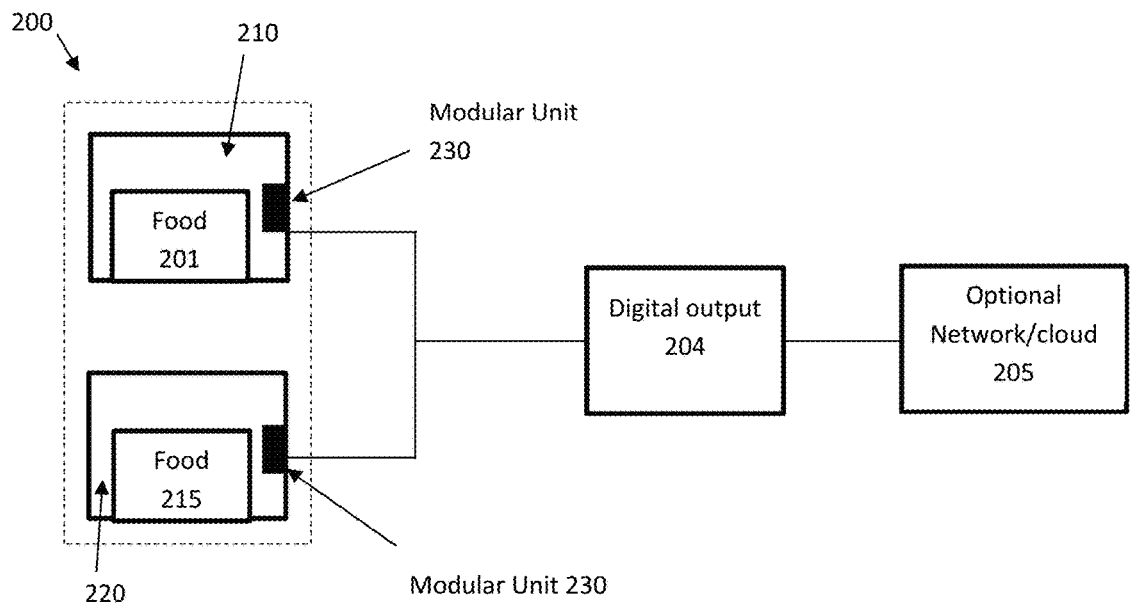
FIG. 2B is a schematic of another embodiment of the microbial growth detection system, or Microbial Activity Detection (MAD) (200) described herein.

The microbial growth detection system, or Microbial Activity Detection (MAD) (200), is illustrated schematically in FIGS. 2A-B. In FIG. 2A, 201 represents the perishable product present in a chamber 210, e.g., a refrigerator, package, carton, positioned over, or in proximity of, a wound, etc. A physical or chemical sensor 202 is also present in the chamber. The sensor 202 can comprise a sensor that is designed to detect byproducts of microbial growth including, but not limited to, $CO_2$, ethylene, hydrogen sulfide, ammonia, amines, total volatile nitrogen, and volatile acids and bases. Sensors can be flexible, screen-printed, single sensors or an array of sensors, or immobilized on a substrate, as readily understood to the skilled artisan. In a particularly preferred embodiment, a $CO_2$ sensor is used. A detection system 203 is included to permit the detection of changes in the sensor 202. The information from the detection system 203 is digitized and sent to a digital output device 204. The information from the detection system 203 can be sent using a wired format or wireless systems such as WiFi, BLUETOOTH®, or combination thereof. The digital output device 204 interprets or analyzes the data received from the detection system 203, using computer devices and algorithms, and is configured to provide an indication of the extent of microbial growth or the shelf-life status. For example, the digital output device 204 can be configured to display, on an output display, final results in analog (yes/no, green/yellow/red) or digital (food about to go bad or the consumption of a certain food should be prioritized over another food) format on a computer or any smart device. The display can be in multiple languages. The digital output device 204 is optionally connected to a network or a cloud-based system, e.g., for inventory tracking, blockchain, and/or machine learning purposes, as understood by the person skilled in the art.

It is noted from FIG. 2A that a second chamber 220 comprising a perishable product 215, a sensor 202, and a detection system 203, is configured to optionally communicate, via wired formats or wireless systems, with the digital output device 204. It should be appreciated that chamber 201 and chamber 220 can be positioned in a larger, third chamber (shown schematically as a dashed line), or alternatively, chamber 201 and chamber 220 can represent entirely separate chambers. An example of the third chamber could be a refrigerator, wherein chamber 201 and chamber 220 represent two separate chambers that are being monitored within the third chamber refrigerator. Entirely separate chambers could be, for example, two separate refrigerators 201 and 220. It should be appreciated by the person skilled in the art that these are just examples to assist with the understanding of FIG. 2A and are not intended to limit the breadth of the MAD system in any way. It should also be appreciated to the person skilled in the art that perishable product 201 and perishable product 215 can be the same as or different from one another.

Detection systems 203 contemplated include, but are not limited to, at least one of a spectrophotometer, devices that utilize visual inspection, electromotive force (emf) detection, frequency detection, infrared detection, or any combination thereof. Alternative detection systems include, but are not limited to, fluorescent detectors, electrochemical detectors, dye-based detectors, and colorimetric indicator detectors, which are selected based on the byproduct of microbial growth to be detected. In a particularly preferred embodiment, the detection system comprises the emf detection or frequency detection. The detection system 203 further comprises a system that is capable of transmitting the digitized results to the digital output device 204, whether utilizing a wired format or wireless capabilities. In a preferred embodiment, the detection system comprises emf or frequency detection. For example, the detection system can detect turbidity/opacity change in the detector and can correlate the turbidity/opacity to a voltage or frequency measurement (i.e., an electrical signal).

In an embodiment of FIG. 2A, the sensor 202 comprises a cuvette holder for the insertion of a cuvette therein. The detection system 203 comprises a source of EMR, e.g., a LED, a photodetector, e.g., a photoresistor, and an MCU (micro-control unit), wherein the MCU comprises electronic circuitry and computer-executable instructions to digitize the detected changes in the sensor 202 to frequency or electromotive force and permit the relay of the digital data to a digital output device 204. The detection system 202 further comprises an energy source 320 including, but not limited to, batteries, RFID tags, NFID tags, and AC sources.

Although not intending to be bound by a numerical value, the system can be programmed to detect the extent of microbial growth at least one time per day, for example, 2, 3, 4, 5, 6, 7, 8, 9, 10, or more readings per day, as readily determined by the person skilled in the art.

In a first aspect, a system for detecting microbial growth on or in at least one perishable product in real time is described, said system comprising:
 (A) a chemical sensor comprising a cuvette holder for the positioning of a cuvette, wherein the chemical sensor is capable of sensing a byproduct of microbial growth;
 (B) a detection device for measuring at least one characteristic of said chemical sensor and converting the measured characteristic into an electrical signal;

(C) a digital output device capable of receiving the electrical signal from the detection device and algorithmically analyzing the electrical signal; and (D) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user to dispose of, or sterilize, the perishable product. In practice, the system will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion there through, and at least one wall that is optically transparent in the wavelengths employed in the method of using the microbial growth detection system. The detection device further comprises a source of electromagnetic radiation (EMR), such as a light-emitting diode (LED) or IR-emitting diode.

In a preferred embodiment of the first aspect, the system for detecting microbial growth on or in at least one perishable product in real time comprises:

(A) a carbon dioxide sensor comprising a cuvette holder for the positioning of a cuvette, wherein the $CO_2$ sensor is capable of sensing carbon dioxide emanating from the perishable product;

(B) a detection device for measuring turbidity in the $CO_2$ sensor and converting the turbidity into an electrical signal;

(C) a digital output device capable of receiving the electrical signal from the detection device and algorithmically analyzing the electrical signal; and (D) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user to dispose of, or sterilize, the perishable product. In practice, the system will further comprise a cuvette, which is insertable in the cuvette holder, wherein the cuvette comprises at least one species that reacts with the byproduct of microbial growth. For example, when sensing $CO_2$, the at least one species can comprise a aqueous hydroxide solution such as calcium hydroxide. In one embodiment, the cuvette comprises at least one wall comprising a gas-permeable microporous membrane capable of $CO_2$ diffusion there through, and at least one wall that is optically transparent in the wavelengths employed in the method of using the microbial growth detection system. The detection device further comprises a source of electromagnetic radiation (EMR).

Users of the system include, but are not limited to, farmers, processors, distributors, manufacturers, storage operators, transporters, retail stores, food service operations, members of households, and medical service providers.

Advantageously, the microbial growth detection system can detect microbial growth in real time. In some embodiments, the microbial growth detection system can detect microbial growth in situ in real time. The system is compact, sensitive, inexpensive, automated, and easy to use. The system is universal and as such, does not have to be tailored to the perishable product, with the proviso that the size and/or arrangement of the overall system may have to be adapted because of perishable product environment requirements (e.g., a refrigerator versus a wound). Furthermore, the microbial growth detection system can provide an output display, or a response, that is qualitative or quantitative and analog or digital. For example, the response can comprise a color scheme (e.g., green, red, orange, wherein a color indicates whether the food has spoiled), text or numerical data. This output data can be further used for machine learning and artificial intelligence to improve the system and method of using.

Additional advantages associated with the microbial growth system described herein is the ability to trace and manage perishable products, including status alerts and prioritization of activities such as using a particular food before it spoils, changing a bandage on a wound because the microbial growth is excessive, and can be applied in a variety of industries including, but not limited to, food, medicine, medical devices, beauty, and hygiene products. This invention can predict the status of microbial growth in real time by measuring chemicals released during microbial activity. The output from the sensor data can be correlated to the extent of microbial activity, and provide information to the user through, for example, their smart devices.

Further advantages of the microbial system described herein is that no sample preparation or technical training is necessary, and the system can be single use or reusable. It should be appreciated that the chemical species in the chemical sensor may be prepared by the user but in many scenarios, a manufacturer will prepare and provide the chemical species to the user. For example, the system comprises a chemical sensor comprising a cuvette holder for the positioning of a cuvette. The cuvette comprises at least one species that reacts with the byproduct of microbial growth, as discussed further hereinbelow. If the species undergoes an irreversible reaction, the contents of the cuvette cannot be reused. Accordingly, the system comprises a cuvette holder wherein cuvettes comprising fresh chemistries (i.e., reactants for the chemical reaction) can be inserted therein and withdrawn at the completion of the chemical reaction, for reuse of the system.

Modular Unit

Figure 3A:
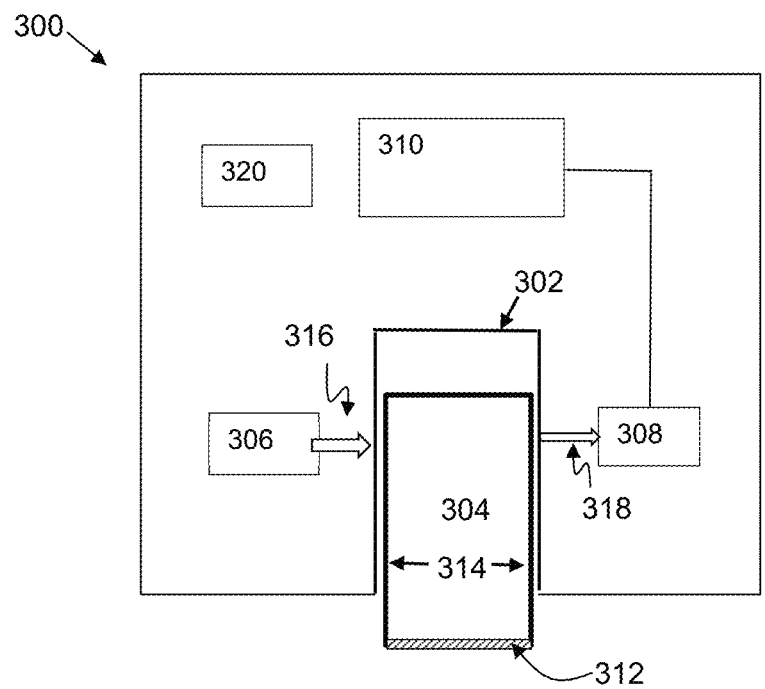
FIG. 3A is a schematic of an embodiment of the modular unit described herein, wherein the cuvette is partially inserted in the cuvette holder.
Figure 3B:
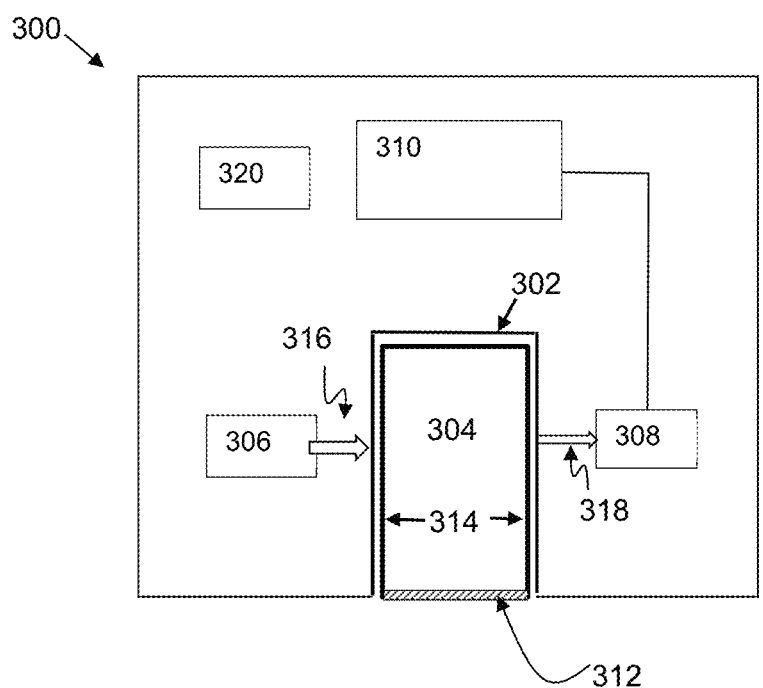
FIG. 3B is a schematic of another embodiment of the modular unit described herein, wherein the cuvette is fully inserted in the cuvette holder.
Figure 3C:
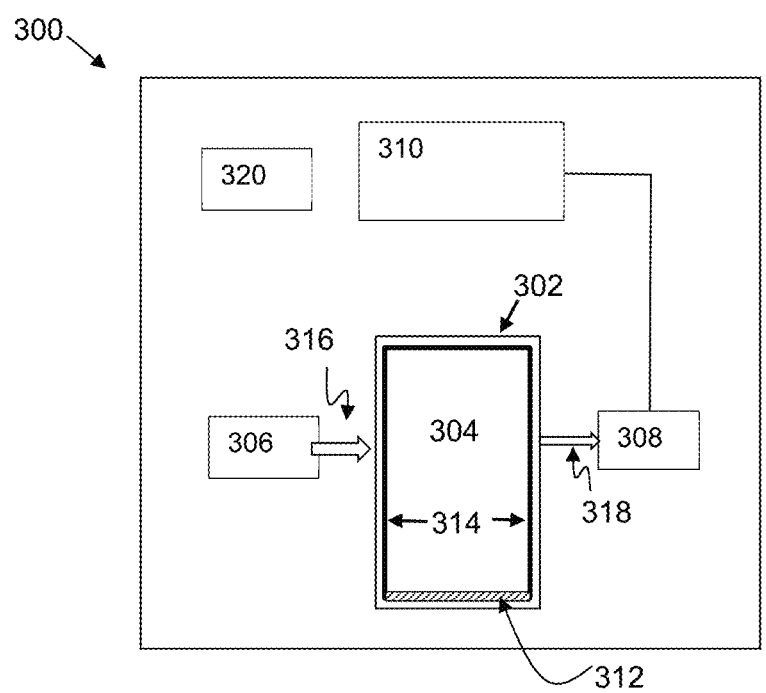
FIG. 3C is a schematic of another embodiment of the modular unit described herein, wherein the cuvette is positioned on the inside of the enclosure of the modular unit.

As introduced hereinabove with reference to FIG. 2A, the detection system 203 is included to permit the detection of changes in the sensor 202. Although shown outside of the chamber 210 in FIG. 2A, the detection system 203 is preferably positioned in a modular unit that also comprises the sensor 202, wherein the modular unit is present inside the chamber 210, 220 (FIG. 2B). Embodiments of the modular unit 300 are illustrated in FIGS. 3A-C. It should be appreciated by the person skilled in the art that the arrangement of the modular unit is not limited to that shown in FIGS. 3A-C, and is intended to be broadly interpreted. The modular unit 300 comprises a cuvette holder 302, wherein the partial insertion of a cuvette 304 in the holder 302 is illustrated in FIG. 3A. The modular unit further comprises a source of EMR 306, e.g., a LED, and a photodetector 308, e.g., a photoresistor. The incident light 316 from the source EMR 306 passes through small cavity (not shown) in the cuvette holder 302 and the walls of the cuvette 304, which are optically transparent in the wavelengths employed in the method of detecting microbial growth, and emerges from another small cavity (not shown) in the cuvette holder as transmitted light 318. The MCU (micro-control unit) 310 comprises electronic circuitry and computer-executable instructions to digitize the relative light opacity (or color) of the solution in the cuvette to frequency or electromotive force and permit the relay of the digital data to a digital output device. The modular unit further comprises an energy source 320 including, but not limited to, batteries, RFID tags, NFID tags, and AC sources. The modular unit 300 preferably comprises an enclosure that minimizes the exposure of the components contained therein to external light and noise, which can interfere with the measurement of the turbidity/opacity of the solution in the cuvette 304.

FIG. 3B illustrates the full insertion of the cuvette in the modular unit of FIG. 3A, wherein the semipermeable membrane of the cuvette is directly exposed to the environment outside of the modular unit. FIG. 3C represents another embodiment of the modular unit, wherein the cuvette holder and cuvette are positioned within the enclosure of the modular unit, wherein the enclosure is fabricated using a material that permits the passage of gases therethrough. It is understood that the enclosure of FIG. 3C may have an access or door to access the cuvette in the event the cuvette is to be replaced for reuse of the modular unit. Alternatively, the enclosure of FIG. 3C can be fully disposable and hence devoid of any access or door to access the inside of the modular unit.

It should be appreciated by the person skilled in the art that although only one wall of the cuvette in FIGS. 3A-3C comprises a gas-permeable microporous membrane capable of byproduct diffusion there through, that the invention is not intended to be limited as such. In one embodiment, at least two walls of the cuvette comprise a gas-permeable microporous membrane capable of byproduct diffusion there through. Further, at least two walls of the cuvette can be optically transparent in the wavelengths employed in the method of using the microbial growth detection system.

The modular unit may optionally incorporate a RFID tag or an SKU tag to allow a user, e.g., a farmer, distributor, consumer, having more than one microbial growth detection systems to identify and monitor the location and current condition of the microbial growth detection system. The RFID tags may communicate with an RFID reader and/or sensor network access point. Each RFID tag may include a controller, a sensor and memory, which are preferably embodied on a single chip, but may also or alternatively include a different type of controller, such as an application specific integrated circuit (ASIC). The RFID tags may optionally be BLUETOOTH®-enabled, ZigBee-enabled, WiFi-enabled, and/or cellular data-enabled.

In one embodiment, the enclosure is made using 3-D printing because of the flexibility of design, although other methods of fabricating the enclosure are contemplated. The size and the shape of the modular unit is entirely dependent on the environment that the modular unit is intended to be placed to sense and detect microbial growth. For example, the unit can be a cubic square or a rectangular parallelepiped with a size in a range from about 3-10 cm×about 3-10 cm×about 3-10 cm, as readily determined by the person skilled in the art. Alternatively, a unique modular unit can be designed and fabricated to specifically fit into a unique environment. For example, with the advent of 3-D printing, any shape and size of the enclosure is easily envisioned. The cuvette holder can accommodate a cuvette having, e.g., a circular cylinder, a cubic square, or a rectangular parallelepiped shape, as readily determined by the person skilled in the art.

As introduced hereinabove, the entire modular unit 230 comprising the sensor and the detection system is preferably positioned inside the chambers 210, 220. An embodiment of this is shown in FIG. 2B.

In a preferred embodiment, the modular unit comprises components that have low energy requirements and that do not emanate a substantial amount of heat during operation. Further, the modular unit can be produced inexpensively and can be adapted to fit in any environment where products undergo microbial growth and spoilage.

Accordingly, a second aspect of the invention relates to a modular unit comprising:
(i) a chemical sensor comprising a cuvette holder for the positioning of a cuvette, wherein the chemical sensor is capable of sensing a byproduct of microbial growth; and
(ii) a detection device for measuring at least one characteristic of said chemical sensor and converting the measured characteristic into an electrical signal.

The detection system can digitize the relative light opacity (or color) of the solution in the cuvette to frequency or electromotive force (i.e., an electrical signal). In practice, the modular unit will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed. The detection device further comprises a source of electromagnetic radiation (EMR), such as a light-emitting diode (LED) or IR-emitting diode.

In a preferred embodiment of the second aspect of the invention, a modular unit comprises:
(i) a $CO_2$ sensor comprising a cuvette holder for the positioning of a cuvette, wherein the $CO_2$ sensor is capable of sensing $CO_2$ gas; and
(ii) a detection device for measuring turbidity in the $CO_2$ sensor and converting the turbidity into an electrical signal.

The detection device can digitize the relative light opacity (or color) of the solution in the cuvette to frequency or electromotive force (i.e., an electrical signal). In practice, the modular unit will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed. The detection device further comprises a source of electromagnetic radiation (EMR), such as a light-emitting diode (LED) or IR-emitting diode.

In a third aspect, a system for detecting microbial growth on or in a perishable product in real time is described, said system comprising:

(A) modular unit comprising:
  (i) a chemical sensor comprising a cuvette holder for the positioning of a cuvette, wherein the chemical sensor is capable of sensing a byproduct of microbial growth; and
  (ii) a detection device for measuring at least one characteristic of said chemical sensor and converting the measured characteristic into an electrical signal;
(B) a digital output device capable of receiving the electrical signal from the detection device and algorithmically analyzing the electrical signal; and
(C) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user to dispose of, or sterilize, the perishable product. In practice, the system will further comprise a cuvette, which is insertable in the cuvette holder, wherein the cuvette comprises at least one species that reacts with the byproduct of microbial growth. In one embodiment, the cuvette comprises at least one wall comprising a gas-permeable microporous membrane capable of byproduct diffusion therethrough, and at least one wall that is optically transparent in the wavelengths employed in the method of using the microbial growth detection system. The detection device further comprises a source of electromagnetic radiation (EMR), such as a light-emitting diode (LED) or IR-emitting diode.

In a preferred embodiment of the third aspect, the system for detecting microbial growth on or in a perishable product in real time comprises:
(A) a modular unit comprising:
  (i) a carbon dioxide sensor comprising a cuvette holder for the positioning of a cuvette, wherein the $CO_2$ sensor is capable of sensing carbon dioxide emanating from the perishable product;
  (ii) a detection device for measuring turbidity in the chemical sensor and converting the turbidity into an electrical signal;
(B) a digital output device capable of receiving the electrical signal from the detection device and algorithmically analyzing the electrical signal; and
(C) an output display, wherein results of the analysis performed by the digital output device are provided to a user, wherein the results convey to the user the extent of microbial growth of the perishable product.

The detection device can digitize the relative light opacity (or color) of the solution in the cuvette to frequency or electromotive force (i.e., an electrical signal). The digital output device uses an algorithm to correlate the electrical signal from the detection device to the extent of microbial growth for the perishable product. Once the extent of microbial growth on or in the perishable product becomes too large, as readily identified by the digital output device using algorithms, the output display is configured to warn the user to dispose of, or sterilize, the perishable product. In practice, the system will further comprise a cuvette, which is insertable in the cuvette holder, wherein the cuvette comprises at least one species that reacts with the byproduct of microbial growth. For example, when sensing $CO_2$, the at least one species can comprise an aqueous hydroxide solution such as calcium hydroxide. In one embodiment, the cuvette comprises at least one wall comprising a gas-permeable microporous membrane capable of $CO_2$ diffusion therethrough, and at least one wall that is optically transparent in the wavelengths employed in the method of using the microbial growth detection system. The detection device further comprises a source of electromagnetic radiation (EMR).

Advantageously, the modular unit of the second and third aspect is based on spectrophotometric principles without requiring the use of a traditional spectrophotometer. Accordingly, it can have a small footprint and can be placed in environments that a traditional spectrophotometer cannot be placed. In addition, the modular unit is simple to use and no sample preparation is needed and as such, the modular unit does not require a specially trained technician to operate same. Moreover, the cost of the modular unit is a fraction of the cost of a traditional spectrophotometer.

An Embodiment of a Sensor

An embodiment of a sensor for the microbial growth detection system includes a chemical sensor, for example, a $CO_2$ sensor. It is possible to reliably detect low amounts of $CO_2$ released during microbial growth in real time from a perishable product. A $CO_2$ sensor exploits the principles of chemical kinetics to produce a change in the appearance of a chemical solution when the carbon dioxide comes in contact with the chemical solution. The output of the sensor can be measured as change in opacity and can be quantified as the concentration of carbon dioxide released from the perishable product during microbial growth.

The $CO_2$ sensor uses a cuvette 304 comprising at least one wall comprising a gas-permeable microporous membrane 312 capable of $CO_2$ diffusion therethrough, and at least one wall that is optically transparent 314 in the wavelengths employed in the method of using the microbial growth detection system. As understood by the person skilled in the art, the shape of the cuvette should substantially correspond to the shape of the cuvette holder in the modular unit so that the cuvette is insertable in the cuvette holder.

The $CO_2$ sensor uses a gas-permeable microporous membrane to permit $CO_2$ gas to contact the chemical solution contained in the cuvette. Preferably, liquids and solids cannot penetrate the microporous membrane. Even more preferably, the microporous membrane is permeable to only $CO_2$ gas. As a result, the acidity or alkalinity of the perishable product does not affect the $CO_2$ sensor. Further, the $CO_2$ sensor is usable with perishable products regardless of the temperature and/or pressure conditions to which they may be subjected during manufacture, handling, and distribution. When fully inserted in the modular unit, only the $CO_2$-permeable microporous membrane 312 is in contact with the environment comprising the perishable product (312). $CO_2$-permeable microporous membranes include, but are not limited to, fluorinated ethylene propylene having a specific gravity of approximately 2, polyvinyl chloride copolymer, any microporous sheet that is $CO_2$-permeable, and commercially available microporous sheets that are colored and are safe for human use. Fluorinated ethylene propylene, also known as TEFLON™, can be selected to have a pore size large enough to pass carbon dioxide gas but too small to pass liquids.

The cuvette, other than the gas-permeable microporous membrane, comprises at least one inert materials selected from plastic, glass, and quartz, preferably quartz. A chemical sensing solution in introduced to the cuvette and the cuvette sealed, wherein the semipermeable membrane is bound to an opening of the cuvette using an adhesive which is impervious to a hydroxide salt and an aqueous solution comprising same. The solution provides a visually observable change when the concentration of $CO_2$ rises substantially above that which is the normal ambient concentration for our atmosphere. In the preferred embodiment, the chemical sensing solution comprises at least one species selected from the group consisting of beryllium hydroxide, calcium hydroxide, magnesium hydroxide, strontium hydroxide, barium hydroxide, ammonium hydroxide, lithium hydroxide, sodium hydroxide, potassium hydroxide, potassium carbonate, sodium barbitol, tribasic sodium phosphate, dibasic sodium phosphate, potassium acetate, monoethanolamine, diethanolamine, piperidine, and any combination thereof, preferably a hydroxide salt, more preferably a Group II hydroxide salt including, but not limited to, beryllium hydroxide, calcium hydroxide, magnesium hydroxide, strontium hydroxide, barium hydroxide, and any combination thereof. In a particularly preferred embodiment, the chemical sensing solution comprises calcium hydroxide, which has USDA approval for human consumption, and which upon contact with $CO_2$, forms calcium carbonate, a milky white precipitate. The concentration of hydroxide salt in the cuvette is in a range from about 0.001 M to about 5 M, preferably about 0.05 M to about 2 M, and more preferably about 0.10 M to about 0.50 M. For example, a molarity of in the concentration range of 0.1-0.5 M $Ca(OH)_2$ requires approximately 5% $CO_2$ gas concentration to initiate precipitation of calcium carbonate. Since the atmospheric concentration of carbon dioxide is approximately 0.3%, atmospheric $CO_2$ will not affect $CO_2$ sensors in the concentration range of 0.1-0.5 M which are left exposed to the air. Further, since the microporous membrane is liquid impermeable, the calcium hydroxide solution will not dry out from storage under exposure to the atmosphere. In one embodiment, said sensor for detecting $CO_2$ is in a concentration range wherein said at least one characteristic, e.g., turbidity, varies in a defined mathematical relationship with an increase in $CO_2$ concentration in said enclosed chamber for the perishable product. The defined relationship is linear, exponential, logarithmic, quadratic, binomial, virial, differential, or a computer-based curve fit.

Because the human eye is unable to adequately quantify the extent of $CaCO_3$ precipitation, i.e., turbidity, the present microbial growth detection system represents a substantial improvement over the prior art, using spectrophotometric principles to detect turbidity. Unlike the spectrophotometers known in the art, which are expensive and bulky, the present system uses a detection system that is robust, inexpensive to make, and can be easily sealed to fit in any environment where products may undergo microbial growth, and hence spoilage. Moreover, using spectrophotometric principles and algorithms, permits the system to quantify the amount of $CO_2$ detected, rather than just visualizing that the solution is opaque, allowing for a more exact determination of whether a perishable product is spoiled or will be spoiled within a certain number of days under the current conditions.

In one embodiment of the described system, the hydroxide salt $CO_2$ sensor described herein does not rely on colorimetric principles, pH-sensitive indicators including, but not limited to, cresol red, metacresol purple, and the like. Put another way, the $CO_2$ sensor in this embodiment is substantially devoid of pH sensitive indicators and color changeable dyes. In another embodiment of the described system, the sensor may utilize colorimetric principles and/or pH-sensitive indicators, as readily understood by the person skilled in the art.

Alternatively, the detection system for the $CO_2$ sensor can detect another characteristic of the reaction including, but not limited to, NTU, milkiness, opalescence, redox potential change, or a color change. Other $CO_2$ sensors contemplated include, but are not limited to, a fluorescent sensor, an electrochemical sensor, a dye-based sensor, and a colorimetric-indicator sensor. The sensor for detecting $CO_2$ is optionally adsorbed onto a substrate.

Advantages of the $CO_2$ sensor described herein includes, but is not limited to, a sensor which is usable on a widest variety of locations, and usable in connection with the widest variety of perishable products, which provides an indication of microbial growth independently of the particular pH of the perishable product; which has a long shelf-life both before and after incorporation into a chamber comprising a perishable product; and which has a compact configuration leading to the widest utilization possible.

Intelligent Bandages

Another source of microbial growth is wounds on patients as the wounds progress towards healing. As defined herein, a "patient" includes human beings, mammals, amphibians, birds, sealife, and plants. Wounds include, but are not limited to, cuts, scrapes, or any other format that exposes the interior of the living matter and has to go through a natural process of healing.

Similar to the system described hereinabove, an intelligent bandage comprising the sensor and the detection device (or the modular unit) is positioned in close proximity to the wound. The sensor can comprise the same components described hereinabove, wherein only USDA approved chemicals are used, e.g., calcium hydroxide. Alternatively, food grade indicators can be used. When using the microbial growth detection system as an intelligent bandage, an analog display such as a color change response is preferred so as to quickly and easily ascertain if the bandage needs to be replaced. The analog display can be provided on the output display. In another embodiment, the intelligent bandage system is configured to provide an analog display on the surface of the bandage. This could be done by including the digital output device and the output display in the modular unit per se.

Notably, because the intelligent bandage comprises the sensor and detection device (or the modular unit) described herein, the intelligent bandage can be fabricated to be relatively small and inexpensive to make. Moreover, with the advent of 3-D printing, the intelligent bandage comprising a modular unit can be fabricated to specifically fit over the specific wound of the patient.

Method of Using

In a fifth aspect, a method for detecting microbial growth on or in a perishable product, is described, said method comprising:
  (I) positioning a chemical sensor and a detection device in a location proximate to the perishable product;
  (II) measuring at least one characteristic of microbial growth on or in the perishable product using the chemical sensor in cooperation with the detection device;
  (III) converting at least one characteristic of the chemical sensor to digitized data;
  (IV) transmitting the digitized data to a digital output device;

(V) algorithmically analyzing the digitized data to determine the extent of microbial growth on or in the perishable product; and
(VI) displaying the extent of microbial growth on an output display to inform a user if the perishable product should be disposed of or sterilized.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over a wound. In a preferred embodiment, the method of detecting microbial growth on or in a perishable product uses any one of the systems described in the first, second, third or fourth aspects described herein. The algorithmic analysis is performed using a computer device. The detection device can digitize the relative light opacity (or color) of the solution in the cuvette to frequency or electromotive force (i.e., an electrical signal).

In another embodiment of the fifth aspect, a method for detecting microbial growth on or in a perishable product, is described, said method comprising:
(I) positioning a carbon dioxide sensor and a detection device in a location proximate to the perishable product;
(II) measuring turbidity in the $CO_2$ sensor using the sensor in cooperation with the detection device;
(III) converting the turbidity to digitized data;
(IV) transmitting the digitized data to a digital output device;
(V) algorithmically analyzing the digitized data to determine the extent of microbial growth on or in the perishable product; and
(VI) displaying the extent of microbial growth on an output display to inform a user if the perishable product should be disposed of or sterilized.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over a wound. In a preferred embodiment, the method of detecting microbial growth on or in a perishable product uses any one of the systems described in the first, second, third or fourth aspects described herein. The algorithmic analysis is performed using a computer device. The detection device can digitize the relative light opacity (or color) of the solution in the cuvette to frequency or electromotive force (i.e., an electrical signal).

In still another embodiment of the fifth aspect, a method for detecting microbial growth on or in a perishable product, is described, said method comprising:
(I) positioning a modular unit in a location proximate to the perishable product, wherein the modular unit comprises a carbon dioxide sensor and a detection device;
(II) measuring turbidity in the $CO_2$ sensor using the sensor in cooperation with the detection device;
(III) converting the turbidity to digitized data;
(IV) transmitting the digitized data to a digital output device;
(V) algorithmically analyzing the digitized data to determine the extent of microbial growth on or in the perishable product; and
(V) displaying the extent of microbial growth on a device that permits the user to conclude if the perishable product can still be used or consumed.

It should be understood by the person skilled in the art that if the amount of bacterial growth on or in the perishable product is above a prescribed threshold that the perishable product should be discarded or sterilized (if possible). The "location" of positioning of the sensor and detection device can be in a chamber as defined herein or can be for example, positioned over a wound. In a preferred embodiment, the method of detecting microbial growth on or in a perishable product uses any one of the systems described in the first, second, third or fourth aspects described herein. The algorithmic analysis is performed using a computer device. The detection device can digitize the relative light opacity (or color) of the solution in the cuvette to frequency or electromotive force (i.e., an electrical signal).

Another aspect of the microbial growth detection system and method of using same is the use of RFID tags/infrastructure to send an alert when perishable products are approaching their expiry date of the maximum permitted amount of microbial growth, thereby establishing communication between consumers and their refrigerators. RFID systems consists of a tag and a scanner and are well known in the art as being able to use the electromagnetic energy to power themselves and send data to the network or cloud-based system. The range of the scanner is up to a few meters. Up to 300 tags/second can be read.

Embodiments of the MAD system and method of using same advantageously provide, for example, sensors, digital output devices, computer devices and computer-readable program products, and related methods to track perishable products from the date of harvest, packaging or shipment, to the date the consumer or restaurant obtains the perishable product, and every stop in between. The technology disclosed herein can utilize a blockchain-based transaction platform to access and track multiple transactions among various parties involved in the growth, manufacture, production, shipment, and storage of the perishable products and its subsequent delivery for consumption to a restaurant or individual household. Any trusted individual or company can access the blockchain-based transaction platform to verify the information associated with any of the records associated with a particular perishable product.

As discussed herein, the sensors of the apparatus include a modular unit that measures various desired parameters, for example the concentration of $CO_2$ in a chamber. The modular unit integrates with the digital output devices which can be configured using the computer-readable program products to directly send the data to the blockchain-based platform.

Determining whether a perishable product is otherwise safe for administration or consumption is one of the main purposes of the MAD systems and method of using same. Quality control and quality assurance of the perishable product is vital. A system comprising a blockchain platform may use a pass or fail system based on a standardization of $CO_2$ levels for the specific perishable product.

Moreover, certain embodiments of the disclosure involve the systems, computer-readable program product, and related computer-implemented methods to obtain information from the users and generate user reports, according to embodiments of the present disclosure as discussed above. These embodiments can be implemented using one or more computers, one or more servers, one or more databases, one or more cloud computing configurations, and one or more communications network Certain embodiments of the disclosure include a system for collecting a plurality of information related to a perishable product and maintaining a database. The plurality of information can also include information from inventory tracking software. The information collected can be used to ensure that the MAD apparatus and method of using same is continually optimized to maximize quality control and quality assurance. Any databases discussed herein may include relational, hierarchical, graphical, blockchain, object-oriented structure and/or any other database configurations. The databases may be organized in any suitable manner, for example, as data tables and/or lookup tables. Each record may be a single file, a series of files, a linked series of data fields or any other data structure.

Because the MAD system is able to track the modular units and the perishable products being monitored by said modular units, the source, location, and destination of the perishable products can be efficiently and effectively identified in the event that the perishable products must be recalled when they, or the same lot, are deemed no longer safe for use or consumption.

It should be appreciated that the MAD system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Various aspects described herein may be embodied as a method, an apparatus, or as computer-executable instructions stored on one or more non-transitory and/or tangible computer-readable media. Any and/or all of the method steps described herein may be embodied in computer-executable instructions stored on a computer-readable medium, such as a non-transitory and/or tangible computer readable medium and/or a computer readable storage medium. Additionally or alternatively, any and/or all of the method steps described herein may be embodied in computer-readable instructions stored in the memory and/or other non-transitory and/or tangible storage medium of an apparatus that includes one or more processors, such that the apparatus is caused to perform such method steps when the one or more processors execute the computer-readable instructions.

Because of the inclusion of computer devices, all data and information can be stored, including information relating to perishable products that were used or disposed of subsequent to a reading.

Advantageously, the microbial growth detection system and method of using same generates information that can allow a user to make informed decisions about food consumption based on the extent of microbial growth, i.e., the freshness indicator. This invention can have economies of scale and can be utilized by everyone in the food supply value chain including, but not limited to, farmers, processors, distributors, storage facilities, as well as in retail stores, food service operations, and households.

It is expected that this invention can be implemented in a wide variety of ways. It will be appreciated that procedures described above are carried out repetitively as necessary. To facilitate understanding, aspects of the invention are described in terms of actions that can be performed by, for example, elements of a programmable computer system or by specialized circuits, by program instructions executed by one or more processors, or by a combination of both.

Thus, the invention may be embodied in many different forms, not all of which are described above, and all such forms are contemplated to be within the scope of the invention. It is emphasized that the terms "comprises" and "comprising," when used in this application, specify the presence of stated features, steps, or components and do not preclude the presence or addition of one or more other features, steps, components, or groups thereof.

The particular embodiments described above are merely illustrative and should not be considered restrictive in any way. The scope of the invention is determined by the following claims, and all variations and equivalents that fall within the range of the claims are intended to be embraced therein.

What is claimed is:

1. A method for detecting microbial growth on or in a perishable product in real time, said method comprising:
   (I) positioning a chemical sensor and a detection device in a location proximate to the perishable product, wherein the chemical sensor comprises a cuvette holder;
   (II) measuring at least one characteristic of microbial growth on or in the perishable product using the chemical sensor in cooperation with the detection device;
   (III) converting at least one characteristic of microbial growth to digitized data;
   (IV) transmitting the digitized data to a digital output device;
   (V) algorithmically analyzing the digitized data to determine the extent of microbial growth on or in the perishable product; and
   (VI) displaying the extent of microbial growth on an output display to inform a user if the perishable product should be disposed of or sterilized,
   wherein a cuvette can be inserted in the cuvette holder, wherein the cuvette comprises at least one wall comprising a gas-permeable microporous membrane capable of byproduct diffusion therethrough, and at least one wall that is optically transparent in the wavelengths employed by a source of electromagnetic radiation.

2. The method of claim 1, wherein the chemical sensor detects a byproduct of microbial growth, wherein said byproduct is selected from the group consisting of carbon dioxide, oxygen, ethylene, hydrogen sulfide, ammonia, volatile and non-volatile amines, total volatile nitrogen, volatile acids and bases, non-volatile acids and bases, slime formation, *E. coli*, *Salmonella*, and *Listeria monocytogenes*.

3. The method of claim 1, wherein the at least one characteristic is selected from the group consisting of Nephelometric Turbidity Units (NTU), milkiness, turbidity, opalescence, redox potential change, light intensity change, and color change.

4. The method of claim 1, wherein the detection device can digitize the at least one characteristic to a frequency or an electromotive force.

5. The method of claim 3, wherein the sensor is a CO2 sensor and the at least one characteristic is turbidity, wherein the detection device can digitize the relative light opacity of the CO2 sensor to a frequency or an electromotive force.

6. The method of claim 1, wherein digital output device correlates the digitized data from the detection device to the extent of microbial growth in or on the perishable product.

7. The method of claim 1, wherein the chemical sensor and the detection device are both housed in a modular unit.

8. The method of claim 7, wherein the modular unit further comprises a source of electromagnetic radiation, a photodetector, a micro-control unit (MCU), and an energy source.

9. The method of claim 1, wherein the chemical sensor is capable of sensing a byproduct of microbial growth.

10. The method of claim 1, wherein the optically transparent wall(s) comprise a material selected from the group consisting of plastic, glass, and quartz.

11. The method of claim 1, wherein the gas-permeable microporous membrane comprises fluorinated ethylene propylene or polyvinyl chloride copolymer or any microporous sheet that is CO2-permeable.

12. The method of claim 1, wherein the cuvette comprises at least one chemical species that reacts with the byproduct of microbial growth.

13. The method of claim 12, wherein the at least one chemical species is selected from the group consisting of beryllium hydroxide, calcium hydroxide, magnesium hydroxide, strontium hydroxide, barium hydroxide, ammonium hydroxide, lithium hydroxide, sodium hydroxide, potassium hydroxide, potassium carbonate, sodium barbitol, tribasic sodium phosphate, dibasic sodium phosphate, potassium acetate, monoethanolamine, diethanolamine, piperidine, and any combination thereof.

14. The method of claim 13, wherein the concentration of the chemical species is in a range from about 0.001 M to about 5 M.

15. The method of claim 1, wherein the output display conveys to the user the extent of microbial growth qualitatively and/or quantitatively, using an analog or digital display.

16. The method of claim 15, wherein the output display comprises a format selected from the group consisting of a smartphone, a tablet, or a laptop computer.

17. The method of claim 1, wherein the digital output device is connected to a network or stored in a cloud.

18. The method of claim 1, wherein the perishable product is selected from the group consisting of chilled and minimally processed foods and beverages, fresh produce, precut produce, cooked food, uncooked food, dairy products, grains, meat, poultry, oils, waxes, roots, nuts, seafood, pharmaceuticals, supplements, solutions, ayurvedic remedy, pharmaceuticals, blood, beauty and hygiene products, medical aids, medical devices, and combinations thereof.

19. The method of claim 1, wherein the electrical signal is electromotive force or frequency.

20. A method for detecting microbial growth on or in a perishable product in real time, said method comprising using a microbial growth detection system to detect a byproduct of microbial growth, said system comprising:

(A) a chemical sensor comprising a cuvette holder for the positioning of a cuvette, wherein the chemical sensor is capable of sensing a byproduct of microbial growth, wherein the cuvette comprises at least one wall comprising a gas-permeable microporous membrane capable of byproduct diffusion therethrough, and at least one wall that is optically transparent in the wavelengths employed by a source of electromagnetic radiation;

(B) a detection device for measuring at least one characteristic of said chemical sensor and converting the measured characteristic into an electrical signal;

(C) a digital output device capable of receiving the electrical signal from the detection device and algorithmically analyzing the electrical signal; and (D) an output display, wherein results of the analysis performed by the digital output device are provided to a user, wherein the results convey to the user the extent of microbial growth of the perishable product.

* * * * *